United States Patent [19]
Jentzen

[11] Patent Number: 5,902,269
[45] Date of Patent: May 11, 1999

[54] LOW DEAD SPACE, INTERCHANGEABLE NEEDLE SYRINGE

[76] Inventor: S. William Jentzen, 3000 Artesian Dr., Cedar Creek, Tex. 78612

[21] Appl. No.: 09/053,771

[22] Filed: Apr. 1, 1998

Related U.S. Application Data

[62] Division of application No. 08/756,241, Nov. 26, 1996, Pat. No. 5,782,803.

[51] Int. Cl.⁶ ........................................ A61M 5/00
[52] U.S. Cl. ............................. 604/110; 604/218
[58] Field of Search ................... 604/110, 218, 604/220–222, 187, 240–243

[56] References Cited

U.S. PATENT DOCUMENTS

| | | |
|---|---|---|
| 3,491,757 | 1/1970 | Arce .......................................... 604/242 |
| 5,256,151 | 10/1993 | Chul .......................................... 604/241 |
| 5,458,576 | 10/1995 | Haber et al. ......................... 604/218 X |
| 5,512,054 | 4/1996 | Morningstar ......................... 604/218 X |
| 5,779,668 | 7/1998 | Grabenkort ......................... 604/218 X |

*Primary Examiner*—John D. Yasko
*Attorney, Agent, or Firm*—Beirne Maynard & Parsons, LLP

[57] ABSTRACT

A non-reusable syringe is provided which has an interchangeable needle, and, further, which has very low residual medication in the syringe after use. Devices for achieving the interchangeable needles while maintaining low residual medication are disclosed.

3 Claims, 6 Drawing Sheets

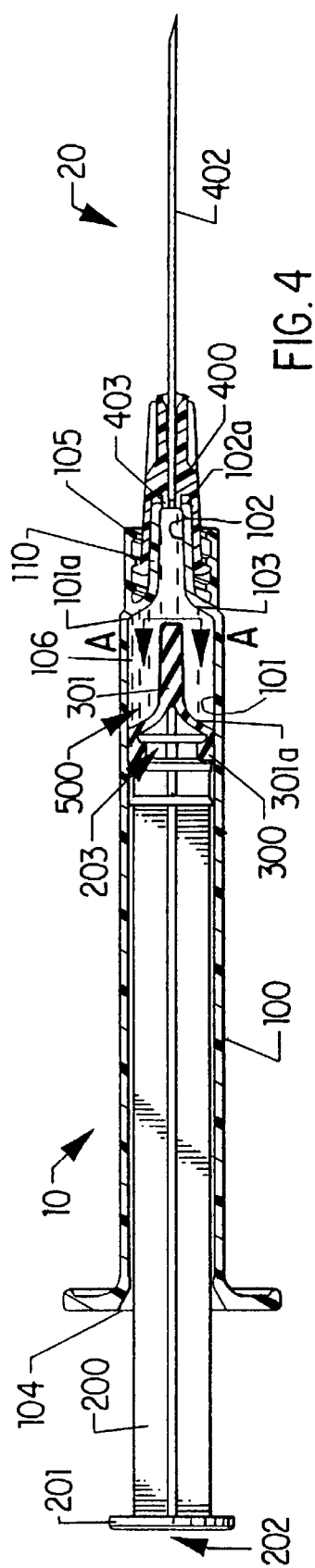
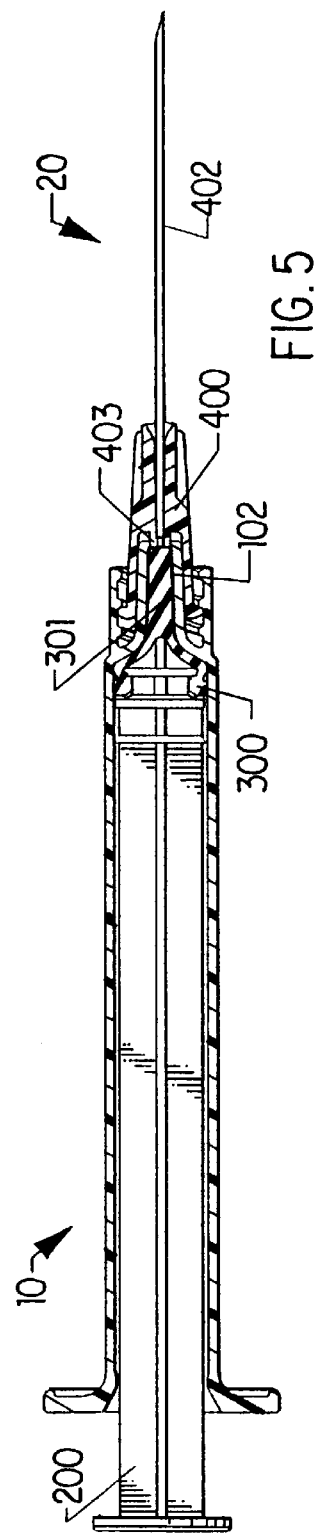
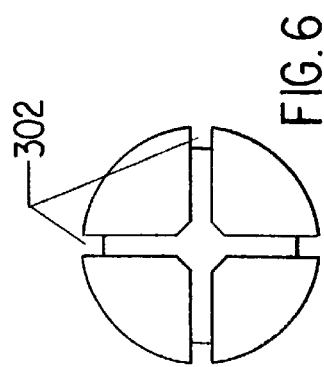

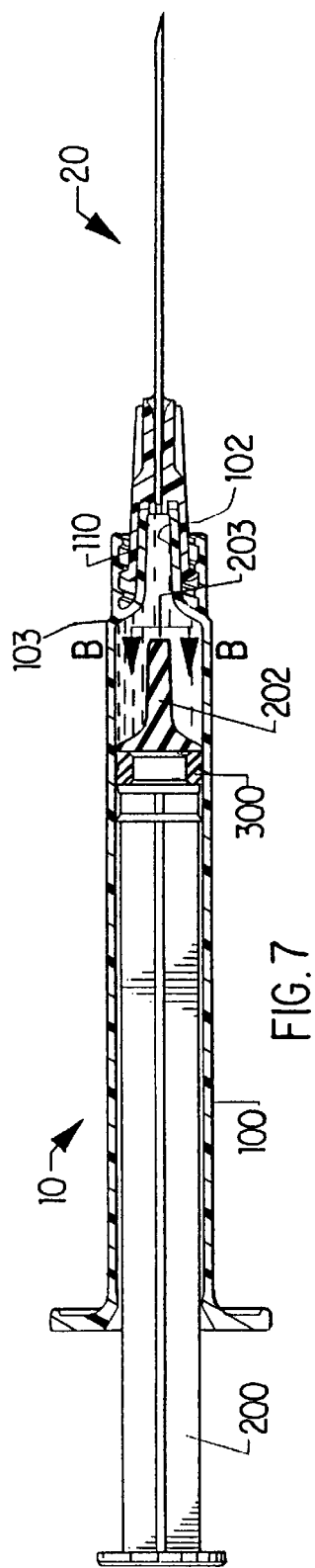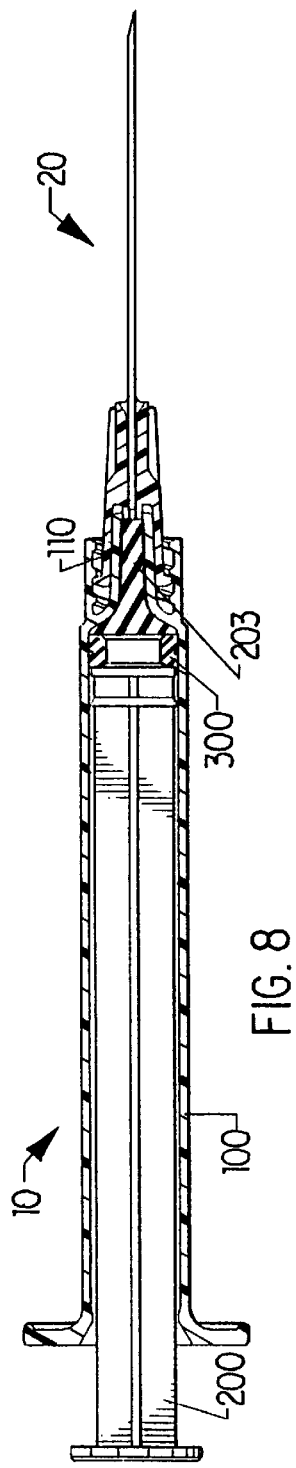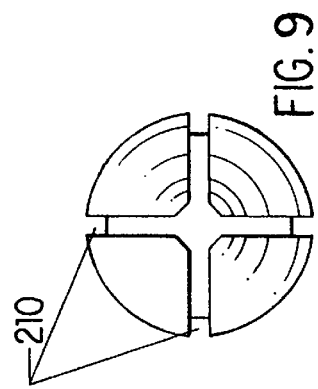

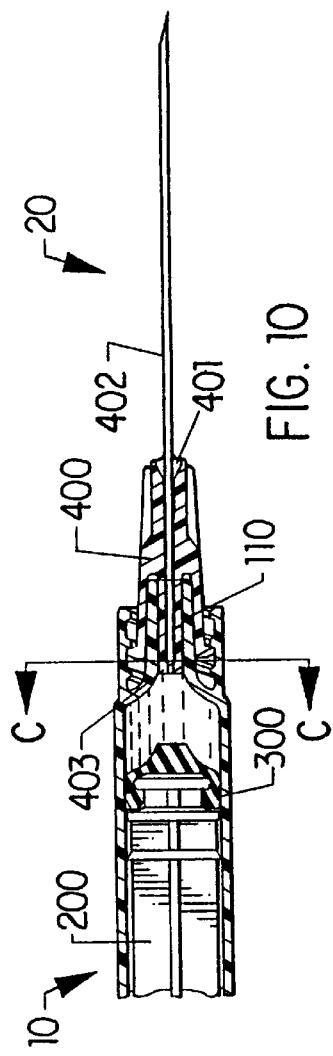
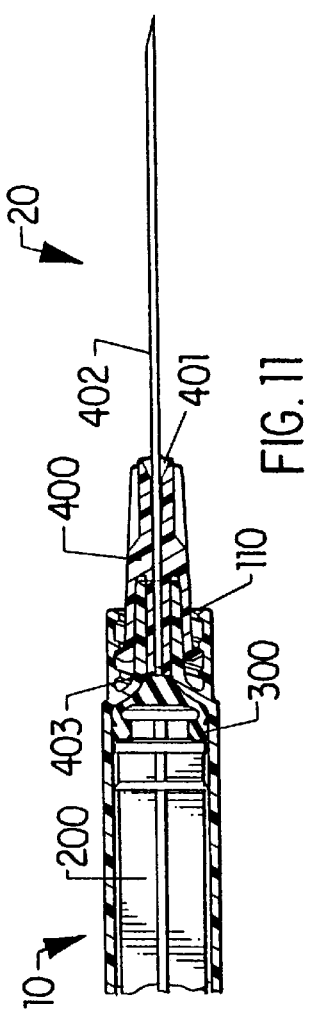
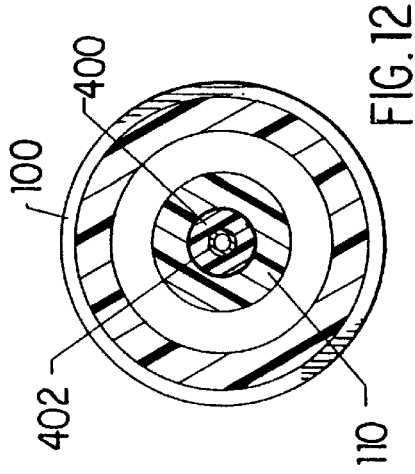

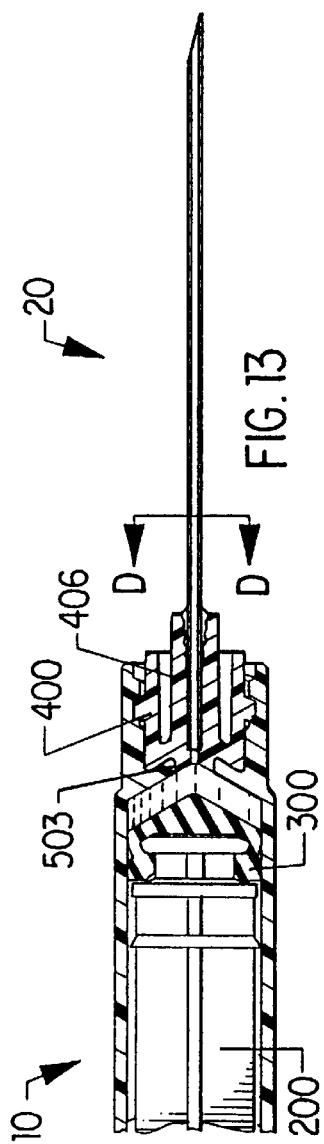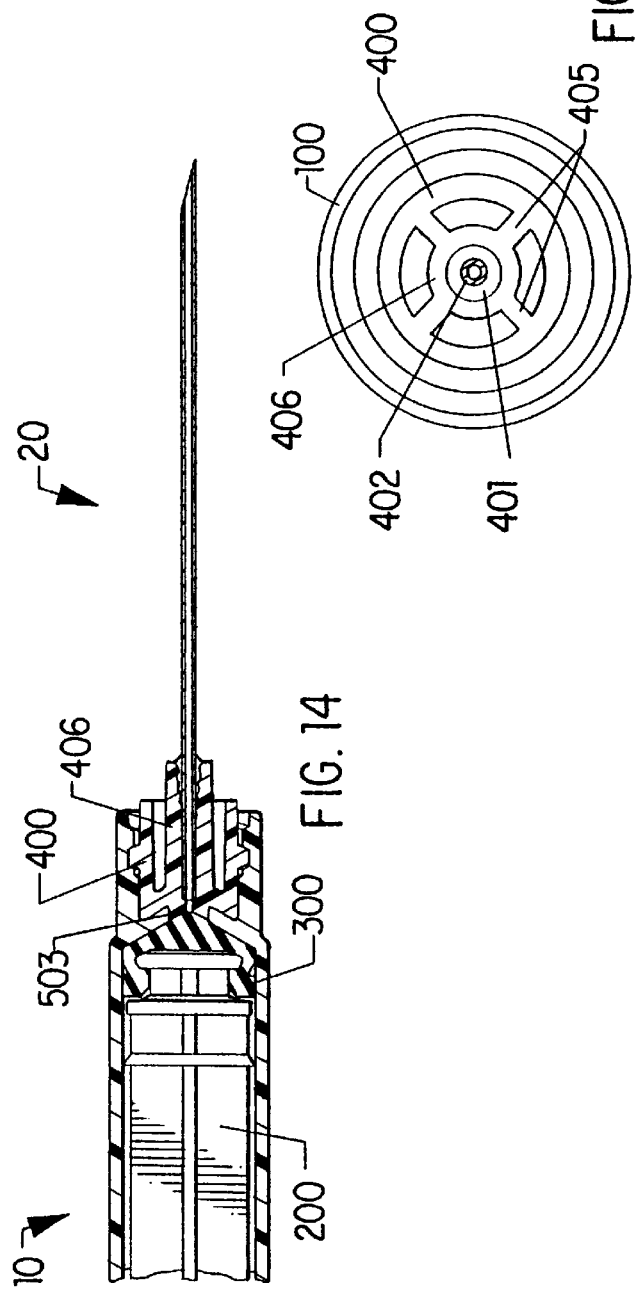

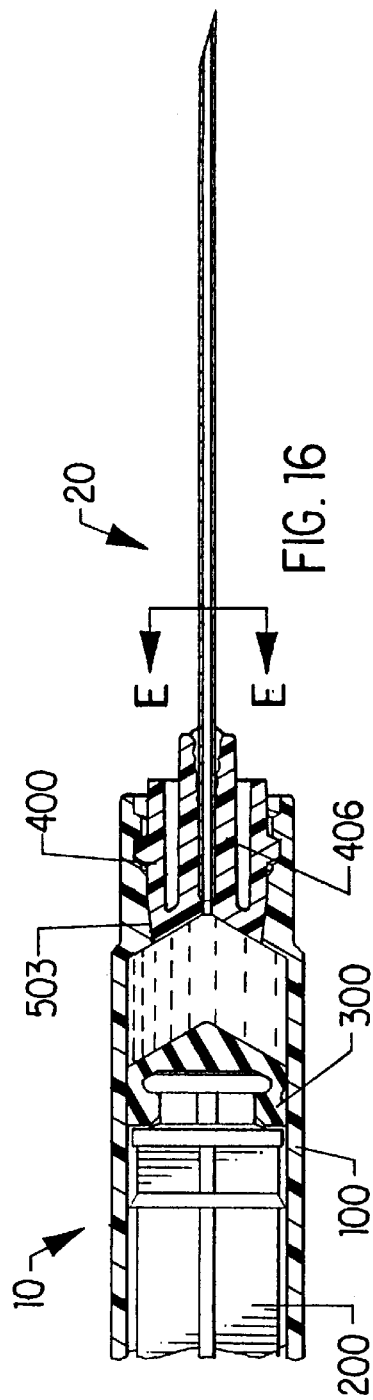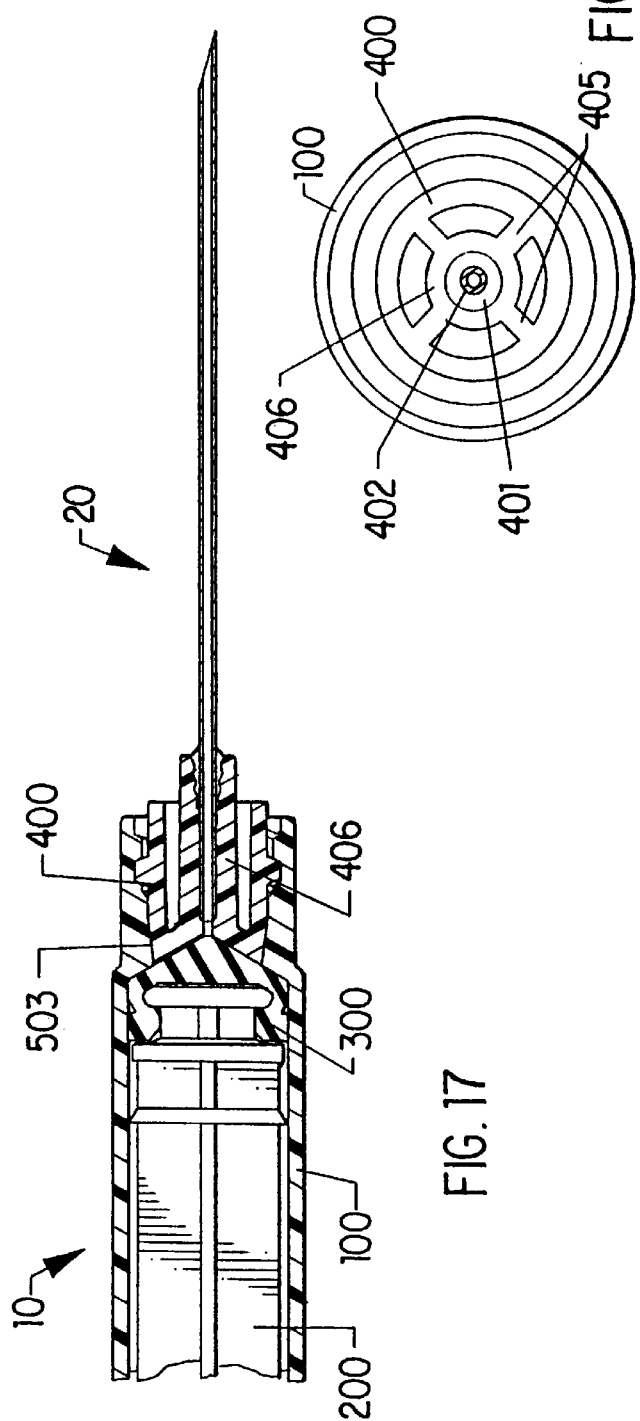

LOW DEAD SPACE, INTERCHANGEABLE NEEDLE SYRINGE

CROSS-REFERENCE TO RELATED APPLICATION

This application is a divisional application of U.S. Ser. No. 08/756,241, entitled: "Low Dead Space, Interchangeable Needle Syringe," filed Nov. 26, 1996 now U.S. Pat. 5,782,803.

BACKGROUND OF THE INVENTION

1. Field of the Invention

This invention relates to a syringe device and, more particularly, to a disposable syringe having an interchangeable needle arrangement while retaining very little fluid following an injection.

2. Description of the Prior Art

The increasing costs of health care have generated many efforts to reduce the cost of devices used to deliver those services. In the case of syringes, a major component of the cost of delivering an injection is often the medication involved. This cost typically far exceeds the purchase price of the syringe itself.

Most of the prior art in the United States utilizes an interchangeable needle assembly known as a "Luer" fitting. This fitting consists of a tapered conical nozzle at the distal end of the barrel, and is most often accompanied by a threaded collar to secure a mating needle assembly to the nozzle. Without the threaded collar the assembly is referred to as a "slip tips", and with the threaded collar the assembly is referred to as a "Luer lock" tip.

Because of the shape of this conical fitting, and the mating recess on the needle assembly, significant amounts of medication are still present in the mating assembly following an injection. It is not uncommon for there to be 0.08 milliliters of medication still in the assembly following an injection. For a 1.00 milliliter injection, this amounts to an extra 8% medication consumed unnecessarily.

An alternative arrangement currently marketed in the United States forgoes the interchangeable needle assembly and permanently attaches the needle to the syringe in such a way that there is very little residual medication. However, this is less desirable because there are a large number of combinations of barrel capacities, needle diameters and needle lengths in use today. For a healthcare facility to carry all permutations in fixed needle format is very expensive. Most healthcare facilities would prefer to carry the components and then mate them as needed.

There is a need to provide healthcare workers with "the best of both worlds"—low residual medication and needle interchangeability.

SUMMARY OF THE INVENTION

The present invention provides an interchangeable needle, disposable syringe with very low residual medication ("dead space"). A cylindrical barrel is provided which includes first and second ends. The barrel has a first internal wall of a given diameter and a second internal wall having an internal diameter smaller than the diameter of the first internal diameter wall. The second internal diameter wall has an end which protrudes distally away from the distal end of the first internal diameter wall.

A chamber is provided for receipt of fluid within the barrel and between the first and second barrel ends. A plunger is extendable into the barrel through the first end of the barrel with the plunger having a distal and dorsal end. The plunger is selectively moveable from an expanded position to an expended position. A low dead space sealing means is included which has an elastomeric sealing member which is engaged to the plunger immediate the distal end of the plunger for slidable sealing contact with at least one of the first and second internal walls of the barrel. An elongated nose tip portion, sometimes provided in the form of a blunt-ended nose tip portion, is slidable along and extending distally through the second internal wall of the barrel. In the case of the blunt-ended nose tip configuration, this nose tip extends distally to but not through the second internal wall of the barrel.

The syringe may also include a third inwardly sloping, curved internal diameter surface extending between the first and second barrel internal diameter walls. The low dead space sealing means may also include a sealing portion of the sealing member profile for selective contourly snug contact along the third internal diameter wall of the plunger.

The syringe may also include means for selective securement of the hollow needle assembly to the barrel immediate the second and internal end of the barrel.

A Luer-configured securing means may be provided for selectively engaging the hollow needle assembly relative to the barrel. The syringe may also include as a component thereof the hollow needle assembly which is either selectively engaged to one end of the barrel, or may accompany the syringe and be secured to one end of the barrel subsequent to manufacture and prior to use.

The syringe sealing element nose tip may include at least one fluid flow channel defined on the exterior of the elongated nose tip portion for transmission of fluid out of the chamber when the plunger is being moved from the expanded position toward the expended position.

In one embodiment, the needle assembly may have a housing portion extending into the barrel along the second internal diameter wall of the plunger. The blunt ended nose tip portion of the sealing means is moved towards and has effective contact with the housing of the needle assembly extending within the barrel when the plunger is moved toward expended position.

A hollow needle is secured by a variety of means, including adhesive (such as epoxy) or ultrasonic insertion, into a plastic hub, or housing, which is detachable from the barrel. Other means are used to reduce and/or minimize the amount of residual medication in the syringe.

BRIEF DESCRIPTION OF THE DRAWINGS

FIG. 4 is a horizontal, sectional view of the device of the present invention showing a preferred means for minimizing residual medication while maintaining needle interchangeability. Further, the device is shown with the plunger partially withdrawn to make the components more clearly visible.

FIG. 5 is a horizontal, sectional view of the device of FIG. 4, depicted after completion of the injection to show the absence of dead space.

FIG. 6 is a cross sectional view of the device of FIG. 4 taken along lines A—A of FIG. 4.

FIG. 7 is a horizontal sectional view of an alternative preferred means for minimizing residual medication while maintaining needle interchangeability. Further, the device is shown with the plunger partially withdrawn to make the components more clearly visible.

FIG. 8 is a horizontal, sectional view of the device of FIG. 7, depicted after completion of the injection to show the absence of dead space.

FIG. 9 is a cross sectional view of the device of FIG. 7 taken along lines B—B of FIG. 7.

FIG. 10 is a partial horizontal sectional view of yet another alternative preferred means for minimizing residual medication while maintaining needle interchangeability. Further, the device is shown with the plunger partially withdrawn to make the components more clearly visible.

FIG. 11 is a horizontal, sectional view of the device of FIG. 10, depicted after completion of the injection to show the absence of dead space.

FIG. 12 is a cross sectional view of the device of FIG. 10 taken along lines C—C of FIG. 10.

FIG. 13 is a partial horizontal sectional view of yet another alternative preferred means for minimizing residual medication while maintaining needle interchangeability. Further, the device is shown with the plunger partially withdrawn to make the components more clearly visible.

FIG. 14 is a horizontal, sectional view of the devise of FIG. 13, depicted after completion of the injection to show the absence of dead space.

FIG. 15 is a cross sectional view of the device of FIG. 13 taken along lines D—D of FIG. 13.

FIG. 16 is a partial horizontal sectional view of yet another alternative preferred means for minimizing residual medication while maintaining needle interchangeability. Further, the device is shown with the plunger partially withdrawn to make the components more clearly visible.

FIG. 17 is a horizontal, sectional view of the device of FIG. 16, depicted after completion of the injection to show the absence of dead space.

FIG. 18 is a cross sectional view of the device of FIG. 16 taken along lines E—E of FIG. 16.

DESCRIPTION OF THE PREFERRED EMBODIMENTS

Figure 1:
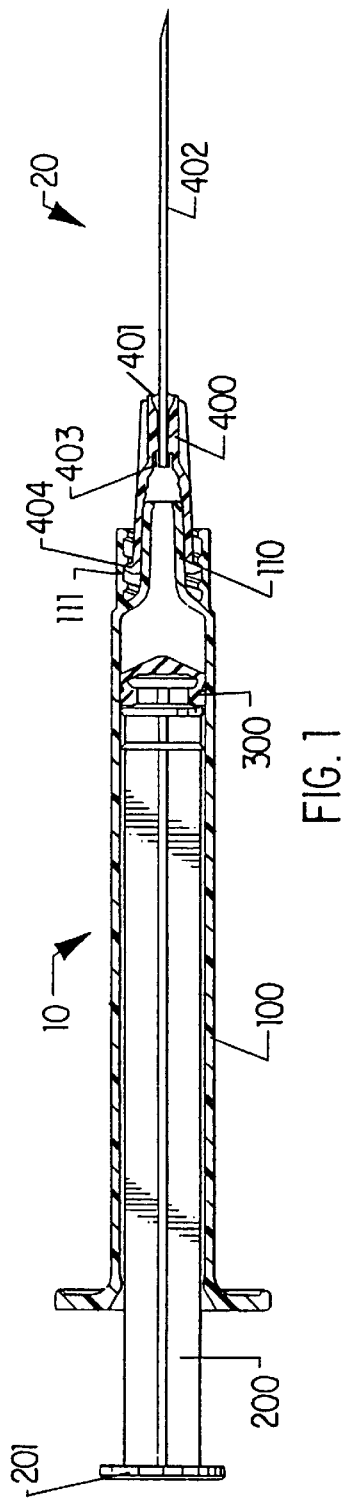
FIG. 1 is a horizontal, sectional view of an example of the prior art prior to usage and, further, prior to the introduction of medication therein.

Now, with first reference to FIG. 1, a prior art syringe barrel assembly 10 is shown with an elongated barrel element 100 interiorly receiving a plastic plunger 200. Affixed thereto is a sealing element 300, which is made of an elastomeric material so as to provide an effective seal between the movable plunger and the barrel wall. The plastic plunger 200 and barrel 100 are manufactured by known techniques for making such plastic components, but will typically be made through injection molding techniques of a plastic such as polypropylene.

Also as shown in FIG. 1 there is attached thereto a needle assembly 20, consisting of a plastic needle assembly hub 400, a hollow needle 402 with a pointed open end, and an adhesive 401 to secure the two components relative to each other. The hub 400 is also manufactured by known techniques, typically injection molding of polypropylene.

The needle assembly 20 is removably attached to the barrel assembly 10 via a tapered nozzle fitting 110. This male nozzle matches the corresponding female receptacle on the needle hub 400. Around the base of the hub 400 is a thread 404 which may engage companion threads on the Luer lock thread collar 111—if provided.

Figure 2:
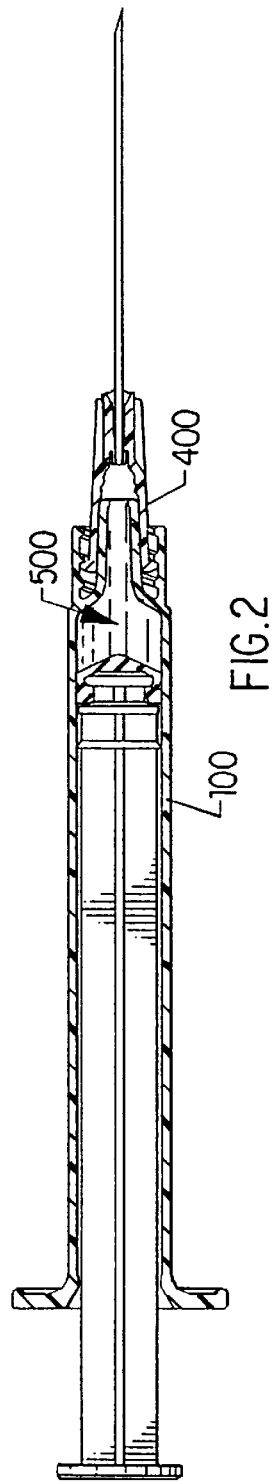
FIG. 2 is a horizontal, sectional view of the prior art of FIG. 1 after medication has been introduced therein.

With reference to FIG. 2, the introduction of medication 500 within the syringe fills the distal end of the syringe barrel 100, as well as a portion of the empty space in the needle hub 400.

Figure 3:
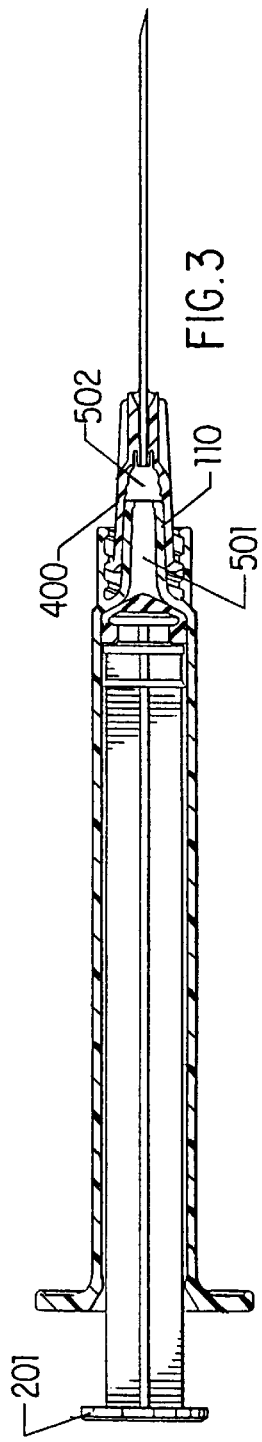
FIG. 3 is a horizontal, sectional view of the prior art of FIGS. 1 and 2, depicted after completion of the injection and indicating the components of dead space.

With reference to FIG. 3, it can be seen that completion of the injection does not remove all of the fluid contained in the interchangeable needle assembly. A portion of the medication remains inside the nozzle 110, hereinafter the "nozzle dead space" 501, and another portion of the medication remains inside the needle hub 400, hereinafter the "hub dead space" 502. This residual medication cannot be removed simply by increasing the amount of axial force applied by the user to the plunger thumbpad 201.

To generally describe the invention, a cylindrical barrel 100 forms a portion of the safety syringe assembly 10. The barrel includes a first end 104 and a second end 105 and further comprises a first internal diameter wall 101 of a given diameter and a second internal wall 102 having an internal diameter wall smaller than the diameter of the first internal diameter wall. The second internal diameter has an end 102A protruding distally away from the distal end 101A of the first internal diameter wall.

A chamber 106 is provided for receipt of fluid 500 within the barrel 100 and between the first and second barrel ends, 104 and 105, respectively. A plunger 200 is extendable into the barrel 100 through the first end 104 of the barrel. The plunger 200 has a distal end 203 and a proximal end 202. The plunger 200 is selectively moveable from an expanded position (FIG. 4) to the expended position (FIG. 5).

Low dead space sealing means include an elastomeric sealing member 300 engaged to the plunger 200 immediate the distal end 203 for slidable sealing engagement with at least one of the first and second internal diameter walls 101, 102 of the barrel 100. An elongated nose tip 301 may be blunt ended for slidable movement along the second internal wall 102 of the barrel 100.

A third inwardly sloping, curved internal diameter surface 103 extends between the first and second barrel internal diameter walls, 101 and 102 with the low dead space sealing means further including a sealing portion 301A of the sealing member profiled for selective contourly snug contact along the third internal diameter wall of the barrel 100.

With specific reference to FIGS. 4, 5 and 6, one preferred embodiment of the present invention consists of elongating the plunger sealing means 300, forming an elongated nose tip 301 in a shape which mates with the nozzle 110 to expel residual medication. As an injection is completed, the shaped tip 301 enters the nozzle 110, displacing almost all medication present. To prevent the sealing means 300 from closing off the nozzle 110 prematurely, one or more small flow channels 302 are placed radially around the tip, as shown in FIG. 6.

Furthermore, it will be appreciated that the prior art needle assembly 20 of FIG. 1 may be mated to the barrel assembly 10 incorporating the plunger 200 of FIG. 4, allowing healthcare workers to achieve a substantial reduction in residual medication-the nozzle dead space—without any change to the needle assemblies they currently utilize.

Additional reductions in residual medication can be achieved by eliminating the hub dead space. In the preferred embodiment of FIG. 4, this is accomplished by moving the needle seat 403 of hub 400 toward the distal end of the plunger nozzle 110 until it is interiorly received within the nozzle. A slightly longer needle is required to achieve the same net length of exposed needle, but the hub 400 of FIG. 4 is also slightly shorter than the hub 400 of FIG. 1. In any event, the adhesive (or other bonding means) which bonds needle 402 to hub 400 remains in the same location, and of the same amount, as in FIG. 1.

It will also be appreciated from FIG. 4 that a healthcare worker could mate the needle assembly 20 of the present invention to a standard barrel assembly (10 of FIG. 1), and achieve the benefits of reduced hub dead space while not discarding any traditional syringe barrel assemblies on hand.

Now with respect to FIGS. 7, 8 and 9, there is shown an alternative preferred means for reducing residual medication while maintaining needle interchangeability. The same needle assembly 20 of FIG. 4 is utilized and mated to the barrel nozzle 110 as before. Instead of the sealing means adopting the shape of the nozzle, however, the plunger end 202 is elongated in a fashion to match the barrel second internal diameter 102. To maintain the necessary seal between the plunger 200 and the barrel 100, the sealing means 300 is reduced to a twin-lobed, elastomeric donut which rides in a recess on the plunger. As the plunger reaches the bottom of its stroke, the shaped end 202 enters the nozzle 110 and displaces almost all of the medication. As shown in FIG. 9, flow channels 210 are again present on the plunger end 202 to avoid sealing off the nozzle prior to full expulsion of the medication.

With reference to FIGS. 10, 11 and 12 there is shown yet another preferred embodiment of the invention. In this embodiment, the interior taper angle of the nozzle 110 has been reduced to zero, while the exterior taper angle is unchanged. The needle seat 403 of hub has been elongated, so that it now rests at the point inside the nozzle where the sealing means 300 will just come in contact with it—thereby expelling almost all residual medication. The adhesive (or other bonding means) 401, however, remains at the distal end of the hub 400 to facilitate assembly. While typically a taper-free nozzle will cause difficulties in removing the part from an injection mold, the relatively short length of this section, coupled with the small diameter, will minimize ejection difficulties. FIG. 12 depicts the close fit between the needle hub 400 and the nozzle 110.

With reference to FIGS. 13, 14 and 15 there is shown yet another preferred embodiment of the invention. In this embodiment the standard Luer nozzle is removed and a custom seal 503 is created between the barrel assembly 10 and needle assembly 20. This allows the hub 400 to be shortened dramatically. While hub 400 is quite small, it can be molded of a fairly stiff plastic, such as polypropylene, to endure the stresses placed upon it during use of the product. As shown in FIG. 15, the stem 406 and needle 402 are maintained in axial alignment via three or more struts 405 and the adhesive 401 (or other bonding means).

With reference to FIG. 16 there is shown still another preferred embodiment of the invention. As in FIG. 13, the standard Luer nozzle is removed. In this case, however, the seal 503 is formed using a reverse taper. Instead of tapering down as it approaches the distal end of the barrel 100, the taper reverses—expanding towards the end of the barrel. Like the seal shown in FIG. 13, the hub 400 is quite a small part. The center stem 406 is therefore likely be supported through the use of struts as depicted in FIG. 18.

Although the invention has been described in terms of specified embodiments which are set forth in detail, it should be understood that it is by illustration only and that the invention is not necessarily limited thereto, since other alternative embodiments and operating techniques will become apparent to those skilled in the art in view of the disclosure. Accordingly, modifications are contemplated which can be made without departing from the spirit of the described invention

What is claimed and desired to be secured by Letters Patent is:

1. A low dead space safety syringe, comprising:

(a) a cylindrical barrel including first and second ends, and comprising a first internal diameter wall portion extending to an inwardly protruding straight wall portion having angled first and second face sections;

(b) a chamber for receipt of medicinal fluid within said barrel;

(c) a plunger extendable into said barrel and being selectively moveable from an expanded position to an expended position;

(d) a hollow needle assembly selectively securable to the interior of the barrel in abutting relationship with the second face section of the inwardly protruding straight wall section; and (e) dead space sealing means including an elastomeric sealing member engaged with the plunger immediate the distal end of the plunger for slidable sealing contact with the first internal diameter wall of said barrel and further including angled outer surface members for sealing contact with an angled first face section of the straight wall section of the cylindrical barrel.

2. The syringe of claim 1 wherein at least one fluid flow channel is defined on the exterior of the dead space sealing means, for transmission of fluid out of the chamber when the plunger is moved from the expanded position to the expended position.

3. The syringe of claim 1 wherein fluid flow channel means are defined on the exterior of the low dead space sealing means for transmission of fluid out of the chamber when the plunger is moved between the expanded position and the expended position, said fluid flow channel means including a series of radially spaced horizontal and intersecting vertical channel members.

* * * * *